(12) United States Patent
Kuwahara et al.

(10) Patent No.: US 7,364,668 B2
(45) Date of Patent: Apr. 29, 2008

(54) PROCESS FOR PRODUCING AN AMINO COMPOSITION

(75) Inventors: Hisayuki Kuwahara, Kanagawa (JP); Tsutomu Numoto, Okayama (JP); Masatoshi Echigo, Kanagawa (JP); Shun Ogawa, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 538 days.

(21) Appl. No.: 11/002,063

(22) Filed: Dec. 3, 2004

(65) Prior Publication Data

US 2005/0137424 A1 Jun. 23, 2005

(30) Foreign Application Priority Data

Dec. 17, 2003 (JP) ............................. 2003-418941

(51) Int. Cl.
*C09K 3/00* (2006.01)
(52) U.S. Cl. .................. 252/182.13; 95/162; 203/95; 528/500; 564/512
(58) Field of Classification Search ................ 203/95; 252/182.13; 95/162
See application file for complete search history.

(56) References Cited

U.S. PATENT DOCUMENTS

| 4,039,581 | A | * | 8/1977 | Frulla et al. ................. 564/332 |
| 6,562,934 | B2 | * | 5/2003 | Yonehama et al. ......... 528/122 |
| 6,632,959 | B2 | * | 10/2003 | Inui et al. .................... 560/238 |
| 2002/0055605 | A1 | | 5/2002 | Yonehama et al. |
| 2003/0063002 | A1 | | 4/2003 | Okamoto et al. |
| 2003/0112192 | A1 | | 6/2003 | King et al. |

FOREIGN PATENT DOCUMENTS

| GB | 807623 | * | 1/1959 |
| WO | WO 02/095870 A | | 11/2002 |
| WO | WO 03/096478 A | | 11/2003 |

* cited by examiner

*Primary Examiner*—Mark Eashoo
*Assistant Examiner*—Peter F Godenschwager
(74) *Attorney, Agent, or Firm*—Wenderoth, Lind & Ponack, L.L.P.

(57) ABSTRACT

The present invention provides a process for producing an amino composition by addition reaction between a polyamine and an unsaturated hydrocarbon compound in the presence of a strongly basic alkali metal catalyst to obtain an amino composition containing not more than 2% by weight of unreacted polyamine and preferably not more than 10 ppm of alkali metal.

8 Claims, No Drawings

PROCESS FOR PRODUCING AN AMINO COMPOSITION

BACKGROUND OF THE INVENTION

1) Field of the Invention

The present invention relates to a process for producing an amino composition by addition reaction between a polyamine and an unsaturated hydrocarbon compound. The amino composition obtainable by the process according to the present invention has reactivity with epoxy resins, isocyanates and the like, and is useful as curing agents for epoxy resins or chain extenders for polyurethane resins.

2) Related Art

An amino composition obtained by the addition reaction of a polyamine with an unsaturated hydrocarbon compound has low viscosity and is useful for the reason that, for example, an epoxy resin composition which contains curing agents for epoxy resins comprising said amino composition provides an epoxy resin cured product excellent in various properties.

The process for producing the above-mentioned amino composition by addition reaction between a polyamine and an unsaturated hydrocarbon compound in the presence of a strongly basic alkali metal catalyst has been publicly known (Japanese Patent Kokai No. 2002-161076).

The amino composition obtainable by the process directed in the above Japanese Patent Publication, however, generally contains unreacted polyamine as a residual. When the amino composition contains such residual unsaturated polyamine, an epoxy resin composition using the amino composition as an epoxy resin curing agent may have such defects that the appearance of a coating film tends to be inferior by the phenomena of whitening or tackiness because carbamate or carbonate of polyamine may easily be produced by absorbing carbon dioxide or water vapor in the atmosphere. Especially, the carbamate produced in the case of using metaxylylenediamine as a polyamine is readily crystallized and the phenomenon of whitening tends to occur easily.

It has been known that reducing the content of unreacted polyamine in the amino composition is effective for recovering such defects of the amino composition. As a general method for reducing the content of unreacted polyamine, it is possible to increase the reaction ratio of the unsaturated hydrocarbon compound to the polyamine.

However, in the case of using the amino composition thus obtained as an epoxy resin curing agent, for example, such amino composition has defects not only that the amount of the amino composition as a curing agent to be blended in an epoxy resin may become large, but also that the reaction point of the amino composition to be reacted with epoxy groups of an epoxy resin may be reduced which will cause that the network structure in an epoxy resin cured product may not be formed sufficiently and the satisfactory properties can not be obtained.

On the other hand, unreacted polyamine contained in the amino composition can be removed by using methods such as vacuum distillation. However, polyamines useful for curing agents generally have high boiling point. Therefore, in order to remove unreacted polyamine to the degree wherein the appearance of coating films can be improved sufficiently using a usual method of distillation under reduced pressure, distillation under a high temperature or under highly reduced pressure may be required.

In general, amines may work undesirable changes such as coloration when various operations are conducted with them under a high temperature. In addition, apparatuses requiring high vacuum condition such as a thin-film evaporator are usually expensive. From the above view points, it has been expected to develop another convenient method for removing unreacted polyamine.

Moreover, shortly after being produced, the amino composition usually expresses a transparent liquid having low viscosity. However, regardless of the presence of unreacted polyamine, the amino composition may change over time (for example, increase of viscosity and/or generation of white solid may occur), which may cause not only the remarkable deterioration of commercial value of the amino composition but also the deterioration of physical properties of an epoxy resin cured product derived from an epoxy resin composition containing said amino composition. Therefore, development of a method for producing an amino composition excellent in storage stability has been expected.

SUMMARY OF THE INVENTION

An object of the present invention is to provide a process for producing an amino composition by an addition reaction of a polyamine with an unsaturated hydrocarbon compound, whereby an amino composition having improved properties is obtainable, more specifically, an amino composition excellent in the appearance of a coating film of an epoxy resin composition wherein the phenomena of whitening and/or tackiness may not occur easily and excellent in storage stability wherein changes such as the increase of viscosity and/or the generation of white solid may not occur during the long-term storage and physical properties of epoxy resin cured products may not be deteriorated.

As a result of extensive studies, the inventors have found that, by subjecting a reaction liquid obtained by addition reaction between a polyamine and an unsaturated hydrocarbon compound to steam stripping, unreacted polyamine can be removed selectively from the obtainable amino composition without unfavorable changes such as deterioration or coloration, and also have found that an amino composition excellent in storage stability can be obtained by reducing the residual alkali metal content not more than 10 ppm by means of removing a strongly basic alkali metal catalyst used for said addition reaction during the process, and have accomplished the present invention.

Therefore, the present invention provides a process for producing an amino composition described in the following 1) to 8).

1) A process for producing an amino composition by addition reaction between a polyamine and an unsaturated hydrocarbon compound in the presence of a strongly basic alkali metal catalyst to obtain an amino composition containing not more than 2% by weight of unreacted polyamine, which at least comprises the following steps:

(A) a step of conducting addition reaction between a polyamine and an unsaturated hydrocarbon compound in the presence of a strongly basic alkali metal catalyst to obtain a reaction liquid containing an amino composition (addition reaction-step), (B) a step of removing unreacted polyamine from the reaction liquid containing an amino composition obtained by said addition reaction-step (A) in the form of a mixture of water and unreacted polyamine by steam stripping to obtain an amino composition wherein the content of unreacted polyamine is not more than 2% by weight (steam stripping-step).

2) The process according to (1), which further comprises a step of removing a strongly basic alkali metal catalyst or the alkali metal compound thereof to reduce the content of alkali metal in said amino composition to 10 ppm or less (catalyst-removing-step) to obtain an amino composition containing not more than 2% by weight of unreacted polyamine and not more than 10 ppm of alkali metal.

3) The process according to (2), which at least comprises the following steps:

(A') a step of firstly conducting addition reaction between a polyamine and an unsaturated hydrocarbon compound in the presence of a strongly basic alkali metal catalyst to obtain a reaction liquid containing an amino composition (addition reaction-step), and then removing said strongly basic alkali metal catalyst from said reaction liquid to reduce the content of alkali metal in said reaction liquid to 10 ppm or less (catalyst-removing-step), (B) a step of removing unreacted polyamine from said reaction liquid containing alkali metal not more than 10 ppm obtained by said step (A') in the form of a mixture of water and unreacted polyamine by steam stripping to obtain an amino composition wherein the content of unreacted polyamine is not more than 2% by weight and the content of alkali metal is not more than 10 ppm (steam stripping-step).

4) The process according to (2), which at least comprises the following steps:

(A) a step of conducting addition reaction between a polyamine and an unsaturated hydrocarbon compound in the presence of a strongly basic alkali metal catalyst to obtain a reaction liquid containing an amino composition (addition reaction-step), (B) a step of firstly removing unreacted polyamine from said reaction liquid containing an amino composition obtained by said step (A) in the form of a mixture of water and unreacted polyamine by steam stripping to obtain a reaction liquid containing an amino composition wherein the content of unreacted polyamine is not more than 2% by weight (steam stripping-step), and then removing hydroxide derived from said strongly basic alkali metal catalyst from said reaction liquid containing an amino composition wherein the content of unreacted polyamine is not more than 2% by weight to obtain an amino composition wherein the content of unreacted polyamine is not more than 2% by weight and the content of alkali metal is not more than 10 ppm (catalyst-removing-step)

5) The process according to (1) to (4), wherein said polyamine is selected from the group consisting of polyamines represented by the formula (1) wherein A is a phenylene group or a cyclohexylene group.

$$H_2N-CH_2-A-CH_2-NH_2 \qquad (1)$$

6) The process according to (1) to (4), wherein said polyamine is selected from the group consisting of polyamines represented by the formula (2) wherein n is 2 to 5.

$$H_2N-(CH_2CH_2NH)_n-H \qquad (2)$$

7) The process according to (1) to (4), wherein said polyamine is selected from the group consisting of cyclic aliphatic polyamines having at least nine carbon atoms, at least two amino groups and at least three active hydrogen atoms derived from said amino groups.

8) The process according to (1) to (4), wherein said unsaturated hydrocarbon compound is selected from the group consisting of a cyclic unsaturated hydrocarbon compound having at least one benzene ring and/or cyclohexane ring and a straight-chain unsaturated hydrocarbon compound having 2 to 10 carbon atoms.

DETAILED DESCRIPTION OF THE INVENTION

The process for producing an amino composition of the present invention comprises a step of addition reaction between a polyamine and an unsaturated hydrocarbon compound in the presence of a strongly basic alkali metal catalyst.

1. Polyamines

Suitable polyamines to be used in the present invention include polyamines represented by the formula (1) wherein A is a phenylene group or a cyclohexylene group, polyamines represented by the formula (2) wherein n is 2 to 5, cyclic aliphatic polyamines having at least nine carbon atoms, at least two amino groups and at least three active hydrogen atoms derived from said amino groups, and polyoxyalkylenepolyamines.

$$H_2N-CH_2-A-CH_2-NH_2 \qquad (1)$$

$$H_2N-(CH_2CH_2NH)_n-H \qquad (2)$$

Suitable polyamines represented by the formula (1) include orthoxylylenediamine, metaxylylenediamine, paraxylylenediamine, 1,2-bis(aminomethyl)cyclohexane, 1,3-bis(aminomethyl) cyclohexane and 1,4-bis(aminomethyl) cyclohexane.

Suitable polyamines represented by the formula (2) include diethylenetriamine, triethylenetetramine, tetraethylenepentamine and pentaethylenehexamine.

Suitable cyclic aliphatic polyamines having at least nine carbon atoms, at least two amino groups and at least three active hydrogen atoms derived from said amino groups include menthanediamine, isophoronediamine, diaminodicyclohexylmethane, bis(4-amino-3-methylcyclohexyl) methane, N-aminomethylpiperazine, norbornanediamine and bis(aminomethyl)tricyclodecane.

Suitable polyoxyalkylenepolyamines include polyoxyalkylenediamines such as polyoxyethylenediamine, polyoxypropylenediamine, polyoxytetramethylenediamine and poly(oxyethylene-oxypropylene)diamine; and polyoxyalkylenetriamines such as polyoxyethylenetriamine and polyoxypropylenetriamine.

Among the polyamines described above, metaxylylenediamine is most preferable. In the case of using metaxylylenediamine as a polyamine, in general, the amino composition obtainable by the conventional method may cause the phenomenon of whitening on a coating film of epoxy resin cured products containing said amino composition particularly easily. The amino composition obtainable by the process according to the present invention using metaxylylenediamine as a polyamine brings a remarkable improvement in the appearance of a coating film of epoxy resin cured products. Therefore, the process according to the present invention using metaxylylenediamine as a polyamine can demonstrate the effect of the present invention most remarkably.

2. Unsaturated Hydrocarbon Compounds

Examples of the unsaturated hydrocarbon compounds to be used in the present invention include any kind of hydrocarbon compounds having at least one alkenyl group. Among them, a cyclic unsaturated hydrocarbon compound having at least one benzene ring and/or at least one cyclohexane ring and a straight-chain unsaturated hydrocarbon compound having 2 to 10 carbon atoms are preferable.

Suitable unsaturated hydrocarbon compounds include ethylene, propylene, butene, butadiene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene, divinylbenzene, vinylcyclohexane and divinylcyclohexane.

Among the above suitable unsaturated hydrocarbon compounds, cyclic unsaturated hydrocarbon compounds having at least one benzene ring and/or at least one cyclohexane ring are more preferable. Among them, styrene is most preferable.

3. Strongly Basic Alkali Metal Catalyst

In the process for producing an amino composition of the present invention, alkali metal catalysts exhibiting strong basicity are used. The strongly basic alkali metal catalysts to be used include alkali metals, alkali metal amides and alkylated alkali metals.

Suitable alkali metals include metallic lithium, metallic sodium and metallic potassium. Suitable alkali metal amides include lithium amide ($LiNH_2$), lithium diisopropyl amide and sodium amide. Suitable alkylated alkali metals include methyl lithium and butyl lithium.

Other suitable catalysts exhibiting strong basicity include lithium methylate, lithium ethylate, sodium ethylate, sodium methylate and potassium methylate.

Among them, alkali metal amides are preferable and lithium amide is more preferable.

4. Addition Reaction-Step

The process for producing an amino composition according to the present invention comprises a step (A) of conducting addition reaction between a polyamine and an unsaturated hydrocarbon compound in the presence of a strongly basic alkali metal catalyst to obtain a reaction liquid containing an amino composition (addition reaction-step).

The addition reaction with an unsaturated hydrocarbon compound is preferably conducted after obtaining a reaction intermediate by firstly conducting a preliminary reaction between a polyamine and a strongly basic alkali metal catalyst.

According to the process in which the unsaturated hydrocarbon compound is added after forming a reaction intermediate by the preliminary reaction of a polyamine and a catalyst, the polyamine and the unsaturated hydrocarbon compound can be contacted after the reactivity of active hydrogen atoms of the polyamine is elevated sufficiently, whereby the addition reaction between the polyamine and the unsaturated hydrocarbon compound can be facilitated.

In the preliminary reaction between a polyamine and a strongly basic alkali metal catalyst, the amount of the strongly basic alkali metal catalyst to be used is preferably 0.05 to 5% by weight, more preferably 0.1 to 3% by weight based upon the total weight of the starting materials.

When the amount of the alkali metal catalyst is less than 0.05% by weight, the reaction rate of the addition reaction between the polyamine and the unsaturated hydrocarbon compound may become extremely low. On the other hand, the increased amount of the catalyst more than 5% by weight may not be economically advantageous because the reaction rate is scarcely increased.

The preferable reaction temperature of the preliminary reaction between the polyamine and the strongly basic alkali metal catalyst is 10 to 140° C., more preferably 50 to 120° C. When the reaction temperature is lower than 10° C., progress of the reaction between the polyamine and the strongly basic alkali metal catalyst may be too slow. On the other hand, the increased reaction temperature higher than 140° C. may not be economically advantageous because the reaction rate is scarcely increased.

The preferable reaction time of the preliminary reaction between the polyamine and the strongly basic alkali metal catalyst is 10 to 360 minutes, more preferably 20 to 120 minutes. When the reaction time is shorter than 10 minutes, the reaction between the polyamine and the strongly basic alkali metal catalyst may not proceed sufficiently. On the other hand, the increased reaction time longer than 360 minutes may not be economically advantageous because the reaction rate is scarcely increased.

The addition reaction after the preliminary reaction between a polyamine and a strongly basic alkali metal catalyst is carried out by adding an unsaturated hydrocarbon compound to the reaction mixture preferably in the form of fractionation supply or continuous supply.

When the strongly basic alkali metal catalyst, the polyamine and the unsaturated hydrocarbon compound are added to the reaction mixture all at once to conduct an addition reaction, a rapid heat generation and/or a formation of a polymer of unsaturated hydrocarbon compounds may occur.

In the case of adding the unsaturated hydrocarbon compound to the reaction mixture in the form of divided supply or fractionation supply, the supply may be fractionated into any number of fractions within the range wherein a polymer of unsaturated hydrocarbon compounds is not formed. The method for the fractionation supply can be selected from known arts and is not specifically limited.

In the case of adding the unsaturated hydrocarbon compound to the reaction mixture in the form of continuous supply, the method for supply is not specifically limited and it can be selected from generally known methods such as a method of adding the unsaturated hydrocarbon compound by using a dropping funnel, a method of adding the unsaturated hydrocarbon compound by using a liquid transfer pump.

The addition reaction by adding an unsaturated hydrocarbon compound to the reaction mixture after the preliminary reaction between the polyamine and the strongly basic alkali metal catalyst is usually carried out at the temperature of 50 to 150° C., more preferably 80 to 100° C.

When the reaction temperature of the addition reaction is lower than 50° C., the reaction rate of the addition reaction between the polyamine and the unsaturated hydrocarbon compound may become too slow. On the other hand, when the reaction temperature of the addition reaction is higher than 150° C., a polymer of the unsaturated hydrocarbon compounds may readily be formed as a by-product.

In the reaction between the polyamine and the unsaturated hydrocarbon compound according to the present invention, the reaction ratio of alkenyl groups of the unsaturated hydrocarbon compound to the amino groups of the polyamine is not specifically limited and can be selected depending on the intended use within the range wherein the alkenyl groups can be reacted theoretically with amino groups of the polyamine as a starting material.

When the reaction ratio of the alkenyl groups of the unsaturated hydrocarbon compound to the amino groups of the polyamine is too small, the amount of residual unreacted polyamine in the amino composition may increase and it will take long time to remove the unreacted polyamine. On the other hand, when the reaction ratio of the alkenyl groups of the unsaturated hydrocarbon compound to the amino groups of the polyamine is too large, polymers of the unsaturated hydrocarbon compounds as a by-product may readily be formed. Consequently, the reaction ratio of the alkenyl groups of the unsaturated hydrocarbon compound to the amino groups of the polyamine is preferably 0.2 to 2.0, more preferably 0.5 to 1.8.

By keeping the reaction temperature as it is for 30 to 120 minutes after the completion of adding the unsaturated hydrocarbon compound, an amino composition having stable properties wherein the content of an unreacted unsaturated hydrocarbon compound is not more than 1% by weight can be obtained.

The amino composition obtained by the process of the present invention is an addition product by the addition reaction between a polyamine and an unsaturated hydrocarbon compound, and is a mixture of one or more amino compounds selected from the group consisting of the following amino compounds; a 1-addition product wherein 1 molecule of the unsaturated hydrocarbon compound is reacted with 1 molecule of polyamine, a 2-addition product wherein 2 molecules of the unsaturated hydrocarbon compound are reacted with 1 molecule of polyamine, a 3-addition product wherein 3 molecules of the unsaturated hydrocarbon compound are reacted with 1 molecule of polyamine, and a 4-addition product wherein 4 molecules of the unsaturated hydrocarbon compound are reacted with 1 molecule of polyamine.

That is, the amino composition of the present invention comprises compounds wherein from one to all of the active hydrogen atom(s) of the amino group(s) in 1 molecule of the polyamine are reacted with the alkenyl group(s) of the unsaturated hydrocarbon compound.

In addition, since the amino composition obtained by the addition reaction-step of the process of the present invention is a product obtained by the addition reaction between the polyamine and the unsaturated hydrocarbon compound, it usually is a mixture containing unreacted polyamine used as a starting material and the like additional to the reaction product which is a mixture of compounds selected from the group of the above-mentioned amino compounds.

5. Steam Stripping-Step

In addition to the above-mentioned step (A) (addition reaction-step), the process according to the present invention further comprises a step (B) of removing unreacted polyamine from the reaction liquid containing an amino composition obtained by the addition reaction-step (A) in the form of a mixture of water and unreacted polyamine by steam stripping to obtain an amino composition wherein the content of unreacted polyamine is not more than 2% by weight (steam stripping-step).

According to the steam stripping-step, unreacted polyamine contained in the reaction liquid containing an amino composition obtained by the addition reaction-step (A) can be removed along with vapor by heating the reaction liquid under reduced pressure and then adding a heated and vaporized solvent. The solvent to be used here is not specifically limited as far as its boiling point is lower than unreacted polyamine and it is not reacted with unreacted polyamine or any reaction products which are selected from the above-mentioned group of amino compounds. The most preferable solvent is water.

The heating temperature and the degree of reduced pressure of the reaction liquid containing an amino composition in the above steam stripping-step can be determined by the boiling point of unreacted polyamine.

If the heating temperature of the reaction liquid containing an amino composition is higher than the boiling point of unreacted polyamine in each degree of reduced pressure, there will be no special problem. However, setting up the heating temperature too high may cause such problems as coloration of the obtained amino composition by heating as well as being economically disadvantageous.

Therefore, the heating temperature should preferably be selected from the range expressed by the following mathematical formula (a):

$$BP-20(° C.) \leq HT \leq BP+40(° C.) \qquad (a)$$

more preferably, from the range expressed by the following formula (b):

$$BP-10(° C.) \leq HT \leq BP+20(° C.) \qquad (b)$$

wherein "BP" represents the boiling point of polyamine as a starting material and "HT" represents the heating temperature of the reaction liquid containing an amino composition.

When the degree of reduced pressure is low and the boiling point of polyamine becomes relatively high, the problem of coloration of the obtained amino composition may occur. Therefore, to be more concrete, the heating temperature of the reaction liquid containing an amino composition is preferably not higher than 200° C., more preferably not higher than 180° C., most preferably not higher than 160° C.

As for the degree of reduced pressure, there will be no problem as long as it is selected from the range wherein the boiling point of unreacted polyamine to be removed shows 200° C. or lower. More preferably, the degree of reduced pressure is selected from the range wherein the boiling point of unreacted polyamine shows 160° C. or lower. More concretely, the most preferable degree of reduced pressure is in the range of 2 to 50 mmHg.

When water is used as the solvent for conducting steam stripping in the above-mentioned step (B), water is introduced in the form of steam and the mixture of water and unreacted polyamine is removed (steam stripping method). Thus, the amino composition can be obtained by removing unreacted polyamine in the form of mixture of water and unreacted polyamine from the reaction liquid containing an amino composition by steam stripping.

The steam pressure when steam is introduced in the reaction apparatus is not specifically limited as long as it is not lower than the degree of reduced pressure in the reaction apparatus. The preferable steam pressure is selected from the range of 980 Pa to 1.5 MPa, more preferably 9.8 kPa to 1 MPa.

The method for introducing steam into the apparatus is not specifically limited. The method of blowing steam into the reaction liquid containing an amino composition directly is preferably used in order to increase the removal efficiency of unreacted polyamine. When blowing steam into the reaction liquid, the shape of a steam inlet is not especially limited, and devising a shape can raise the removal efficiency. For example, using a steam inlet having plural openings can raise the removal efficiency of unreacted polyamine.

Examples of water used as the source of steam in the present invention include industrial water, tap water, ion-exchange water and distilled water. Since impurities contained in water may remain in the amino composition as a result of the removal operation of unreacted polyamine, it is preferable to minimize the content of impurities in water as little as possible. Therefore, it is preferable to select the removal solvent to be used for steam stripping from the group consisting of tap water, ion-exchange water and distilled water wherein the content of impurities is relatively low.

As mentioned above, according to the present invention, it is possible to reduce the residual content of unreacted polyamine in the amino composition not more than 2% by weight, preferably not more than 1.5% by weight, more preferably not more than 1.0% by weight based upon the total weight of the amino composition.

6. Catalyst Removing-Step

In the reaction liquid containing an amino composition obtained by the above-mentioned addition reaction-step of the present invention, alkali metal used as a catalyst for the addition reaction remains. According to the present invention, a step of removing the remaining strongly basic alkali metal catalyst, by modifying it to a readily removable compound thereof if necessary, to reduce the content of alkali metal in the amino composition not more than 10 ppm can be comprised in addition to the above-mentioned addition reaction-step and steam stripping-step.

It is possible to remove the strongly basic alkali metal catalyst from the reaction liquid by filtration and the like to a certain degree. Filtration can be carried out after changing the strongly basic alkali metal catalyst to a readily removable compound thereof (an alkali metal compound) by adding acids such as hydrochloric acid, hydrogen chloride gas and acetic acid; alcohols such as methanol and ethanol; or water. For example, in the case of adding water, the strongly basic alkali metal catalyst is changed to an alkali metal hydroxide thereof which can readily be removed by filtration.

However, the crude amino composition wherein more than a certain amount of these strongly basic alkali metal catalyst or the alkali metal compound thereof is remaining, though being a transparent liquid having low viscosity shortly after being produced, may change over time. For example, increase of viscosity and/or generation of white solid may occur. These changes may cause not only the remarkable deterioration of commercial value of the amino composition but also the deterioration of physical properties of an epoxy resin cured product produced from an epoxy resin composition containing said amino composition.

In this regard, it is desirable to keep the content of alkali metal in the amino composition not more than 10 ppm, preferably not more than 5 ppm, most preferably not more than 3 ppm. Thereby, storage stabilization of the amino composition can be attained.

Examples of the process for removing strongly basic alkali metal catalyst or the alkali metal compound thereof from the amino composition include the following methods (I) to (VII):

(I) a method absorbing the alkali metal by using alkali absorbents, (II) a method using water washing, (III) a method firstly neutralizing the alkali metal by adding acid to generate a salt thereof and then removing the generated salt by filtration, (IV) a method using ion-exchange resins, (V) a method firstly neutralizing the alkali metal by introducing carbon dioxide gas to generate a carbonate thereof and then removing the generated carbonate by filtration, (VI) a method firstly neutralizing the alkali metal by adding acidic aqueous solution to generate a salt thereof, removing the generated salt by filtration and then removing the excess of acid by using acid absorbents, and (VII) a method using acid pyrophosphate such as disodium dihydrogen pyrophosphate.

Among these methods, (I) and (II) are preferable from the viewpoint of easiness of operation and an economical efficiency. These methods can be conducted each. independently or in combination with each other.

Examples of alkali absorbents used for the method (I) of removing the alkali metal using alkali absorbents include any kind of alkali absorbents available, for example, MgO, $Al(OH)_3 \cdot xH_2O$, $1.25\ Mg(OH)_2 \cdot Al(OH)_3 \cdot xCO_3 \cdot yH_2O$, $Al(OH)_3 \cdot NaHCO_3$, $Mg_6Al_2(OH)_{16} \cdot CO_3 \cdot 4H_2O$, $Mg_{4.5}Al_2(OH)_{13} \cdot CO_3 \cdot 3.5H_2O$ and $Mg_{0.7}Al_{0.3}O_{1.15}$.

These alkali absorbents can be used independently or in combination with each other.

The amount of alkali absorbents to be used in the present invention is preferably selected from the range of 1 to 1000 parts by weight per 1 part by weight of strongly basic alkali metal catalyst or the alkali metal compound thereof.

When the amount of alkali absorbents to be used is less than 1 part by weight, it may be difficult to reduce the content of alkali metal in the amino composition to 10 ppm or less, which may cause the properties of the amino composition unstable. On the other hand, when the amount of alkali absorbents to be used is more than 1000 parts by weight, the workload of filtration for removing the used alkali absorbents may become large, and moreover, the quantity of filter cake may be increased which is economically disadvantageous.

Removal of strongly basic alkali metal catalyst or the alkali metal compound thereof by alkali absorbents can be carried out at any time after completing the addition reaction between a polyamine and an unsaturated hydrocarbon compound and changing the strongly basic alkali metal catalyst to a readily removable compound by adding acids such as hydrochloric acid, hydrogen chloride gas and acetic acid, alcohols such as methanol and ethanol or water. Examples of the process for removing the strongly basic alkali metal catalyst or the alkali metal compound thereof from the reaction liquid by alkali absorbents include the following methods;

(i) a method comprising a step of changing the strongly basic alkali metal catalyst to the hydroxide thereof by adding water into the reaction liquid after completion of addition reaction, then adding alkali absorbents into the reaction liquid and stirring it for 30 to 300 minutes at 50 to 150° C., and then conducting filtration with the reaction liquid to remove the alkali absorbents, (ii) a method comprising a step of changing the strongly basic alkali metal catalyst to the hydroxide thereof by adding water into the reaction liquid after completion of addition reaction, then after removing water and removing the hydroxide by filtrating to a certain degree, adding alkali absorbents into the reaction liquid to remove the remaining hydroxide and stirring it for 30 to 300 minutes at 50 to 150° C., and then conducting filtration with the reaction liquid to remove the alkali absorbents.

In the above methods (i) and (ii), when the stirring temperature is lower than 50° C., the absorption reaction with alkali absorbents may not proceed rapidly. On the other hand, when the stirring temperature is higher than 150° C., coloration of the amino composition may occur. When the stirring time is shorter than 30 minutes, the absorption reaction with alkali absorbents may not proceed sufficiently.

On the other hand, when the stirring time is longer than 300 minutes, time required for manufacturing may become too long.

Examples of water used for the above-mentioned method (II) using water washing for removing alkali metal or the compound thereof include industrial water, ion exchanged water and distilled water.

The step of removing the strongly basic alkali metal catalyst by water washing can be inserted at any time after the completion of addition reaction between a polyamine and an unsaturated hydrocarbon compound. Examples of the process for removing the strongly basic alkali metal catalyst by water washing include the following methods;

(i) a method comprising a step of adding water to the reaction liquid after the completion of addition reaction and stirring it for 5 to 60 minutes at 10 to 100° C., then leaving it still to separate the reaction liquid into a layer of the amino composition and a water layer, removing the water layer, and then repeating such operation of liquid separation until the content of alkali metal in the amino composition becomes 10 ppm or less, (ii) a method comprising a step of adding water to the reaction liquid after the completion of addition reaction to change the strongly basic alkali metal catalyst to the hydroxide thereof, then after removing water and removing the hydroxide by filtration to a certain degree, adding water to the reaction liquid again and stirring it for 5 to 60 minutes at 10 to 100° C., then leaving it still to separate the liquid into a layer of the amino composition and a water layer, removing the water layer, and then repeating such operation of liquid separation until the content of alkali metal in the amino composition becomes 10 ppm or less.

When the stirring temperature is lower than 10° C., the viscosity of the amino composition may become relatively high and it may be hard to operate the liquid separation. On the other hand, when the stirring temperature is higher than 100° C., vaporization of water may occur. When the stirring time is shorter than 5 minutes, washing may not be accomplished sufficiently. On the other hand, even if extending the stirring time longer than 60 minutes, the effect may not be much improved whereas time required for manufacturing may become too long.

The amount of water to be used in the above method is preferably 20 to 1000 parts by weight per 100 parts by weights of the amino composition. When the amount of water is less than 20 parts by weight or more than 1000 parts by weight, water and the amino composition may become compatible and it may be difficult to carry out the liquid separation.

In the process according to the present invention, the order relation between the steam stripping-step and the catalyst removing-step to be conducted after the addition reaction-step is not restricted. Either of the steam stripping-step and the catalyst-removing-step may be carried out first.

In the case of firstly conducting the addition reaction-step, then conducting the catalyst removing-step, and then conducting the steam stripping-step, the preferable process of the present invention comprises the following steps;

(A') a step of firstly conducting addition reaction between a polyamine and an unsaturated hydrocarbon compound in the presence of a strongly basic alkali metal catalyst to obtain a reaction liquid containing an amino composition (addition reaction-step), and then removing said strongly basic alkali metal catalyst from said reaction liquid to reduce the content of alkali metal in said reaction liquid to 10 ppm or less (catalyst-removing-step)

(B) a step of removing unreacted polyamine from said reaction liquid containing alkali metal not more than 10 ppm obtained by said step (A') in the form of a mixture of water and unreacted polyamine by steam stripping to obtain an amino composition wherein the content of unreacted polyamine is not more than 2% by weight and the content of alkali metal is not more than 10 ppm (steam stripping-step).

In the reaction liquid obtained after the completion of the addition reaction-step, an amino composition produced by the addition reaction and a strongly basic alkali metal catalyst are contained. The step of removing the strongly basic alkali metal catalyst can be inserted before the removal operation of unreacted polyamine.

In the case of removing the strongly basic alkali metal catalyst before the removal operation of unreacted polyamine, it is possible to remove the strongly basic alkali metal catalyst from the reaction liquid by filtration after changing the strongly basic alkali metal catalyst to a readily removable compound thereof (an alkali metal compound) by adding acids such as hydrochloric acid, hydrogen chloride gas and acetic acid, alcohols such as methanol and ethanol or water. For example, in the case of using alkali metal amide as the catalyst, the alkali metal amide can be changed to a hydroxide thereof which can readily be filtrated by means of adding water.

In addition, in order to remove the alkali metal compound furthermore, it is preferable to use any removal method selected from the above-mentioned methods (I) to (VII).

After removing the strongly basic alkali metal catalyst from the reaction liquid containing an amino composition, unreacted polyamine can be removed in the same manner of steam stripping as mentioned above in the form of a mixture of unreacted polyamine and water from said reaction liquid by steam stripping.

In the case of firstly conducting the addition reaction-step, then conducting the steam stripping-step, and then conducting the catalyst removing-step, the preferable process of the present invention comprises the following steps;

(A') a step of firstly conducting addition reaction between a polyamine and an unsaturated hydrocarbon compound in the presence of a strongly basic alkali metal catalyst to obtain a reaction liquid containing an amino composition (addition reaction-step), (B') a step of removing unreacted polyamine from said reaction liquid containing an amino composition obtained by said step (A) in the form of a mixture of water and unreacted polyamine by steam stripping to obtain an amino composition wherein the content of unreacted polyamine is not more than 2% by weight(steam stripping-step), and then removing hydroxide derived from the strongly basic alkali metal catalyst from said reaction liquid wherein the content of unreacted polyamine is not more than 2% by weight to reduce the content of alkali metal in said reaction liquid to 10 ppm or less (catalyst-removing-step) to obtain an amino composition wherein the content of unreacted polyamine is not more than 2% by weight and the content of alkali metal is not more than 10 ppm.

When unreacted polyamine is removed by steam stripping from a reaction liquid containing an amino composition before conducting removal operation of strongly basic alkali metal catalyst, the strongly basic alkali metal catalyst is decomposed by steam introduced for steam stripping to become hydroxide thereof which is remained in the amino composition. Therefore, in this case, after removing unreacted polyamine in the form of a mixture of unreacted polyamine and water by steam stripping from reaction liquid containing an amino composition obtained in the addition reaction-step, the hydroxide derived from the strongly basic alkali metal catalyst can be removed from the amino composition by means of the above-mentioned removal method of (I) to (VII) to obtain an amino composition wherein the content of alkali metal is not more than 10 ppm.

7. Amino Composition

The amino composition obtainable according to the process of the present invention is a composition containing not more than 2% by weight of unreacted polyamine and, preferably, further containing not more than 10 ppm of alkali metal.

When the above-mentioned amino composition is used as an epoxy resin curing agent, a coating film produced by an epoxy resin composition containing the curing agent is excellent in appearance wherein unfavorable phenomena such as whitening and tackiness may scarcely occur. In addition, the amino composition is excellent in storage stability wherein changes such as the increase of viscosity and/or the generation of white solid may not occur during the long-term storage and physical properties of epoxy resin cured products may not be deteriorated. As a result, the commercial value of the amino composition can be maintained for long time.

It is possible to use a product directly obtained by removing unreacted polyamine and, if necessary, removing the strongly basic alkali metal catalyst or the hydroxide thereof by means of the above-mentioned methods as a finished product.

However, the product usually contains a certain quantity of water in addition to the amino composition. Therefore, the product can be used as a finished product after removing water by the well-known method such as distillation if required. In this case, the removal operation of water can be conducted by reducing the pressure for a certain period of time after stopping the supply of steam in the steam stripping-step.

The amino composition obtainable by the process according to the present invention has reactivity with epoxy resins, isocyanates and the like, and is useful as curing agents for epoxy resins or chain extenders for polyurethane resins.

8. Recovery of Unreacted Polyamine

Unreacted polyamine can be recovered by removing water from the mixture of unreacted polyamine and water which is obtained by removal operation of unreacted polyamine from the reaction liquid containing an amino composition in the above-mentioned steam stripping-step.

The method of removing water from the mixture to be used in the step of recovering unreacted polyamine is not specifically limited and can be selected from the well-known methods. For example, water can preferably be removed from the mixture by distillation or distillation under reduced pressure. Moreover, recovered unreacted polyamine can be further distilled in order to upgrade the purity of recovered polyamine.

By recovering unreacted polyamine in this way, it becomes possible to recycle polyamine and is economically advantageous. In addition, since contamination of waste fluid can be controlled, it is desirable in respect of the consideration to environmental pollution.

PREFERRED EMBODIMENT OF THE INVENTION

The present invention will be described in more detail below, referring to Examples which are not intended to limit the scope of the present invention.

In the following embodiments, a storage stability test was conducted by observing the appearance and measuring the viscosity of each test sample of amino compositions after putting 225 g of each amino composition into a glass container with a cover, then charging nitrogen gas therein, and leaving it still for 1 year in an environmental testing room at 25° C. Evaluation of the storage stability test was carried out by the following criteria;

Good: No change in appearance and viscosity

Poor: Some change in appearance and viscosity

The content of unreacted polyamine and alkali metal in the amino composition obtained are measured by gas chromatography measurement and atomic abstraction method respectively.

EXAMPLE 1

(Step 1)

817.2 g (6.0 mol) of metaxylylenediamine (Molecular Weight; 136.2) manufactured by Mitsubishi Gas Chemical Co., Inc. in Japan (hereinafter, "MXDA"), and 2.9 g (0.13 mol) of lithium amide, a reagent manufactured by Merck KGaA, were charged to a 2 L (liter) flask equipped with an agitator, a thermometer, a nitrogen gas inlet, a dropping funnel and a condenser, and its interior temperature was raised to 80° C. in a nitrogen gas stream with stirring.

Then, keeping the interior temperature at 80° C., 625.2 g (6.0 mol) of styrene, a special grade reagent, manufactured by Wako Pure Chemical Industries, Ltd. in Japan, was added thereto dropwise continuously for 2 hours.

After completion of the dropwise addition of styrene, its interior temperature was maintained to 80° C. for 30 minutes.

Then, 23.4 g (1.3 mol) of distilled water as the amount of 10 times equal mole to the charged lithium amide and 29 g of $2MgO_6SiO_2/xH_2O$, manufactured by Kyowa Chemical Industry Co., Ltd. in Japan, bland name of "KYOWAAD 600s", as an alkali absorbent of the amount of 10 times equal parts by weight to the charged lithium amide were added thereto and stirred for 1 hour. Precipitate in the liquid in flask was removed by filtration, whereby 1453 g of reaction liquid containing an amino composition was obtained. The content of unreacted MXDA in the obtained reaction liquid was 15.8% by weight. The content of Lithium in the obtained reaction liquid was 0.7 ppm.

(Step 2)

1453 g of the reaction liquid obtained by the above step was charged to a 2 L (liter) flask equipped with an agitator, a thermometer, a steam inlet and a condenser, and its interior pressure was reduced to 6.0 kPa. After stirring, the interior temperature was raised to 175° C. by heating.

After the interior temperature was reached to the prescribed temperature, steam with pressure of 49 kPa was introduced into the reaction apparatus and a removal operation of unreacted polyamine was carried out for 3 hours to remove unreacted polyamine in the form of a mixture of unreacted polyamine and water. Then, the introduction of steam was stopped and the interior temperature and the degree of reduced pressure were kept as prescribed for 30 minutes, whereby 1175.4 g of an amino composition A was obtained.

The content of unreacted MXDA in the obtained amino composition was 0.9% by weight. The content of 1-addition product was 53.1% by weight, the content of 2-addition product was 42.0% by weight and the content of 3-addition product was 4.0% by weight. The viscosity of the amino composition A was 66 MPa·s. The storage stability test was carried out with the amino composition A and the result was shown in Table 1.

(Step 3)

The mixture of unreacted polyamine and water which was recovered by being distilled and concentrated in the process of the above removal operation was charged to a separable flask, and then water was removed by distillation whereby 206.2 g of residual was obtained. Purity of MXDA in the residual was 92%.

EXAMPLE 2

(Step 1)

1453 g of reaction liquid containing an amino composition was obtained in the same manner as Example 1.

(Step 2)

1453 g of the reaction liquid thus obtained was charged to a flask similar as the one used in Example 1, and its interior pressure was reduced to 2.0 kPa. After stirring, the interior temperature was raised to 145° C. by heating.

After the interior temperature was reached to the prescribed temperature, steam with pressure of 49 kPa was introduced into the reaction apparatus and a removal operation of unreacted polyamine was carried out for 4 hours to remove unreacted polyamine in the form of a mixture of unreacted polyamine and water. Then, the introduction of steam was stopped and the interior temperature and the degree of reduced pressure were kept as prescribed for 30 minutes, whereby 1175.4 g of an amino composition B was obtained.

The content of unreacted MXDA in the obtained amino composition was 1.2% by weight. The content of 1-addition product was 53.0% by weight, the content of 2-addition product was 41.6% by weight and the content of 3-addition product was 4.2% by weight. The viscosity of the amino composition B was 65 MPa·s. The storage stability test was carried out with the amino composition B and the result was shown in Table 1.

(Step 3)

The mixture of unreacted polyamine and water which was recovered by being distilled and concentrated in the process of the above removal operation was charged to a separable flask, and then water was removed by distillation whereby 201.0 g of residual was obtained. Purity of MXDA in the residual was 94%.

EXAMPLE 3

(Step 1)

1453 g of reaction liquid containing an amino composition was obtained in the same manner as Example 1.

(Step 2)

1453 g of the reaction liquid thus obtained was charged to a flask similar as the one used in Example 1, and its interior pressure was reduced to 4.0 kPa. After stirring, the interior temperature was raised to 165° C. by heating.

After the interior temperature was reached to the prescribed temperature, steam with pressure of 49 kPa was introduced into the reaction apparatus and a removal operation of unreacted polyamine was carried out for 2.5 hours to remove unreacted polyamine in the form of a mixture of unreacted polyamine and water. Then, the introduction of steam was stopped and the interior temperature and the degree of reduced pressure were kept as prescribed for 30 minutes, whereby 1182.4 g of an amino composition C was obtained.

The content of unreacted MXDA in the obtained amino composition was 1.9% by weight. The content of 1-addition product was 52.5% by weight, the content of 2-addition product was 41.9% by weight and the content of 3-addition product was 3.7% by weight. The viscosity of the amino composition C was 66 MPa·s. The storage stability test was carried out with the amino composition C and the result was shown in Table 1.

(Step 3)

The mixture of unreacted polyamine and water which was recovered by being distilled and concentrated in the process of the above removal operation was charged to a separable flask, and then water was removed by distillation whereby 198.5 g of residual was obtained. Purity of MXDA in the residual was 95%.

EXAMPLE 4

(Step 1)

853.2 g (6.0 mol) of 1,3-bis(aminomethyl)cyclohexane (Molecular Weight; 142.2), manufactured by Mitsubishi Gas Chemical Co., Inc. in Japan (hereinafter, "1,3-BAC"), and 3.0 g (0.13 mol) of lithium amide were charged to a flask similar as the one used in Example 1, and its interior temperature was raised to 80° C. in a nitrogen gas stream with stirring.

Then, after stirring the reaction mixture for 120 minutes at 80° C., 625.2 g (6.0 mol) of styrene was added thereto dropwise continuously for 2 hours while keeping the temperature at 80° C.

After completion of the dropwise addition of styrene, its interior temperature was maintained to 80° C. for 60 minutes.

Then, 23.4 g (1.3 mol) of distilled water as the amount of 10 times equal mole to the charged lithium amide and 30.0 g of "KYOWAAD 600s" as an alkali absorbent of the amount of 10 times equal parts by weight to the charged lithium amide were added thereto and stirred for 1 hour. Precipitate in the liquid in flask was removed by filtration, whereby 1430.2 g of reaction liquid containing an amino composition was obtained. The content of unreacted 1,3-BAC in the obtained reaction liquid was 15.1% by weight. The content of Lithium in the obtained reaction liquid was 1.2 ppm.

(Step 2)

1430.2 g of the reaction liquid thus obtained was charged to a flask similar as the one used in Example 1, and its interior pressure was reduced to 6.0 kPa. After stirring, the interior temperature was raised to 145° C. by heating.

After the interior temperature was reached to the prescribed temperature, steam with pressure of 49 kPa was introduced into the reaction apparatus and a removal operation of unreacted polyamine was carried out for 2.0 hours to remove unreacted polyamine in the form of a mixture of unreacted polyamine and water.

Then, the introduction of steam was stopped and the interior temperature and the degree of reduced pressure were kept as prescribed for 30 minutes, whereby 1242.4 g of an amino composition D was obtained.

The content of unreacted 1,3-BAC in the obtained amino composition was 1.6% by weight. The content of 1-addition product was 62.7% by weight, the content of 2-addition product was 33.3% by weight and the content of 3-addition product was 2.4% by weight. The viscosity of the amino composition D was 70 MPa·s. The storage stability test was carried out with the amino composition D and the result was shown in Table 1.

(Step 3)

The mixture of unreacted polyamine and water which was recovered by being distilled and concentrated in the process of the above removal operation was charged to a separable flask, and then water was removed by distillation whereby 215.3 g of residual was obtained. Purity of 1,3-BAC in the residual was 96%.

EXAMPLE 5

(Step 1)

1430.2 g of reaction liquid containing an amino composition was obtained in the same manner as Example 4.

(Step 2)

1430.2 g of the reaction liquid thus obtained was charged to a flask similar as the one used in Example 1, and its interior pressure was reduced to 1.3 kPa. After stirring, the interior temperature was raised to 120° C. by heating.

After the interior temperature was reached to the prescribed temperature, steam with pressure of 49 kPa was introduced into the reaction apparatus and a removal operation of unreacted polyamine was carried out for 1.5 hours to remove unreacted polyamine in the form of a mixture of unreacted polyamine and water.

Then, the introduction of steam was stopped and the interior temperature and the degree of reduced pressure were kept as prescribed for 30 minutes, whereby 1242.4 g of an amino composition E was obtained.

The content of unreacted 1,3-BAC in the obtained amino composition was 0.9% by weight. The content of 1-addition product was 63.1% by weight, the content of 2-addition product was 33.6% by weight and the content of 3-addition product was 2.4% by weight. The viscosity of the amino composition E was 70 MPa·s. The storage stability test was carried out with the amino composition E and the result was shown in Table 1.

(Step 3)

The mixture of unreacted polyamine and water which was recovered by being distilled and concentrated in the process of the above removal operation was charged to a separable flask, and then water was removed by distillation whereby 221.1 g of residual was obtained. Purity of 1,3-BAC in the residual was 92%.

EXAMPLE 6

(Step 1)

412.7 g (4.0 mol) of diethylenetriamine, a special grade reagent manufactured by Kanto Kagaku Co., in Japan (hereinafter, "DETA") and 2.5 g (0.11 mol) of lithium amide were charged to a flask similar as the one used in Example 1, and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2 hours while keeping the temperature at 80° C.

After completion of the dropwise addition of styrene, its interior temperature was maintained to 80° C. for 60 minutes.

Then, 19.8 g (1.1 mol) of distilled water as the amount of 10 times equal mole to the charged lithium amide and 25.0 g of "KYOWAAD 600s" as an alkali absorbent of the amount of 10 times equal parts by weight to the charged lithium amide were added thereto and stirred for 1 hour. Precipitate in the liquid in flask was removed by filtration, whereby 777 g of reaction liquid containing an amino composition was obtained. The content of unreacted DETA in the obtained reaction liquid was 16.3% by weight. The content of Lithium in the obtained reaction liquid was 1.5 ppm.

(Step 2)

777 g of the reaction liquid thus obtained was charged to a flask similar as the one used in Example 1, and its interior pressure was reduced to 13.3 kPa. After stirring, the interior temperature was raised to 140° C. by heating.

After the interior temperature was reached to the prescribed temperature, steam with pressure of 49 kPa was introduced into the reaction apparatus and a removal operation of unreacted polyamine was carried out for 2.0 hours to remove unreacted polyamine in the form of a mixture of unreacted polyamine and water.

Then, the introduction of steam was stopped and the interior temperature and the degree of reduced pressure were kept as prescribed for 30 minutes, whereby 589.5 g of an amino composition F was obtained.

The content of unreacted DETA in the obtained amino composition was 1.9% by weight. The content of 1-addition product was 43.2% by weight, the content of 2-addition product was 45.0% by weight and the content of 3-addition product was 9.9% by weight. The viscosity of the amino composition F was 35 MPa·s. The storage stability test was carried out with the amino composition F and the result was shown in Table 2.

(Step 3)

The mixture of unreacted polyamine and water which was recovered by being distilled and concentrated in the process of the above removal operation was charged to a separable flask, and then water was removed by distillation whereby 128.3 g of residual was obtained. Purity of DETA in the residual was 94%.

EXAMPLE 7

(Step 1)

584.8 g (4.0 mol) of triethylenetetramine, a special grade reagent manufactured by Kanto Kagaku Co., in Japan (hereinafter, "TETA") and 3.0 g (0.13 mol) of lithium amide were charged to a flask similar as the one used in Example 1, and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2 hours while keeping the temperature at 80° C.

After completion of the dropwise addition of styrene, its interior temperature was maintained to 80° C. for 60 minutes.

Then, 23.4 g (1.3 mol) of distilled water as the amount of 10 times equal mole to the charged lithium amide and 30.0 g of "KYOWAAD 600s" as an alkali absorbent of the amount of 10 times equal parts by weight to the charged lithium amide were added thereto and stirred for 1 hour. Precipitate in the liquid in flask was removed by filtration, whereby 997 g of reaction liquid containing an amino composition was obtained. The content of unreacted TETA in the obtained reaction liquid was 16.3% by weight. The content of Lithium in the obtained reaction liquid was 1.5 ppm.

(Step 2)

997 g of the reaction liquid thus obtained was charged to a flask similar as the one used in Example 1, and its interior pressure was reduced to 13.3 kPa. After stirring, the interior temperature was raised to 140° C. by heating.

After the interior temperature was reached to the prescribed temperature, steam with pressure of 49 kPa was introduced into the reaction apparatus and a removal operation of unreacted polyamine was carried out for 2.0 hours to remove unreacted polyamine in the form of a mixture of unreacted polyamine and water.

Then, the introduction of steam was stopped and the interior temperature and the degree of reduced pressure were kept as prescribed for 30 minutes, whereby 826.5 g of an amino composition G was obtained.

The content of unreacted TETA in the obtained amino composition was 1.9% by weight. The content of 1-addition product was 59.8% by weight, the content of 2-addition product was 38.4% by weight and the content of 3-addition product was 1.8% by weight. The viscosity of the amino composition G was 116 MPa·s. The storage stability test was carried out with the amino composition G and the result was shown in Table 2.

(Step 3)

The mixture of unreacted polyamine and water which was recovered by being distilled and concentrated in the process of the above removal operation was charged to a separable flask, and then water was removed by distillation whereby 135.3 g of residual was obtained. Purity of TETA in the residual was 94%.

EXAMPLE 8

(Step 1)

681.2 g (4.0 mol) of isophoronediamine, manufactured by Degussa AG (hereinafter, "IPDA") and 3.3 g (0.14 mol) of lithium amide were charged to a flask similar as the one used in Example 1, and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2.5 hours while keeping the temperature at 80° C.

After completion of the dropwise addition of styrene, its interior temperature was maintained to 80° C. for 60 minutes.

Then, 25.2 g (1.4 mol) of distilled water as the amount of 10 times equal mole to the charged lithium amide and 33.0 g of "KYOWAAD 600s" as an alkali absorbent of the amount of 10 times equal parts by weight to the charged lithium amide were added thereto and stirred for 1 hour. Precipitate in the liquid in flask was removed by filtration, whereby 1085 g of reaction liquid containing an amino composition was obtained. The content of unreacted IPDA in the obtained reaction liquid was 14.6% by weight. The content of Lithium in the obtained reaction liquid was 1.8 ppm.

(Step 2)

1085 g of the reaction liquid thus obtained was charged to a flask similar as the one used in Example 1, and its interior pressure was reduced to 13.3 kPa. After stirring, the interior temperature was raised to 170° C. by heating.

After the interior temperature was reached to the prescribed temperature, steam with pressure of 49 kPa was introduced into the reaction apparatus and a removal operation of unreacted polyamine was carried out for 2.0 hours to remove unreacted polyamine in the form of a mixture of unreacted polyamine and water.

Then, the introduction of steam was stopped and the interior temperature and the degree of reduced pressure were kept as prescribed for 30 minutes, whereby 917.7 g of an amino composition H was obtained.

The content of unreacted IPDA in the obtained amino composition was 1.2% by weight. The content of 1-addition product was 59.8% by weight and the content of 2-addition product was 39.0% by weight. The viscosity of the amino composition H was 168 MPa·s. The storage stability test was carried out with the amino composition H and the result was shown in Table 2.

(Step 3)

The mixture of unreacted polyamine and water which was recovered by being distilled and concentrated in the process of the above removal operation was charged to a separable flask, and then water was removed by distillation whereby 158.3 g of residual was obtained. Purity of IPDA in the residual was 94%.

EXAMPLE 9

(Step 1)

617.2 g (4.0 mol) of norbornanediamine, manufactured by Mitsui Chemicals, Inc. (hereinafter, "NBDA") and 3.1 g (0.14 mol) of lithium amide were charged to a flask similar as the one used in Example 1, and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2.5 hours while keeping the temperature at 80° C.

After completion of the dropwise addition of styrene, its interior temperature was maintained to 80° C. for 120 minutes.

Then, 25.2 g (1.4 mol) of distilled water as the amount of 10 times equal mole to the charged lithium amide and 31.0 g of "KYOWAAD 600s" as an alkali absorbent of the amount of 10 times equal parts by weight to the charged lithium amide were added thereto and stirred for 1 hour. Precipitate in the liquid in flask was removed by filtration, whereby 1085 g of reaction liquid containing an amino composition was obtained. The content of unreacted NBDA in the obtained reaction liquid was 15.5% by weight. The content of Lithium in the obtained reaction liquid was 2.2 ppm.

(Step 2)

1085 g of the reaction liquid thus obtained was charged to a flask similar as the one used in Example 1, and its interior pressure was reduced to 1.3 kPa. After stirring, the interior temperature was raised to 120° C. by heating.

After the interior temperature was reached to the prescribed temperature, steam with pressure of 49 kPa was introduced into the reaction apparatus and a removal operation of unreacted polyamine was carried out for 2.0 hours to remove unreacted polyamine in the form of a mixture of unreacted polyamine and water.

Then, the introduction of steam was stopped and the interior temperature and the degree of reduced pressure were kept as prescribed for 30 minutes, whereby 860.3 g of an amino composition I was obtained.

The content of unreacted NBDA in the obtained amino composition was 1.6% by weight. The viscosity of the amino composition I was 108 MPa·s. The storage stability test was carried out with the amino composition I and the result was shown in Table 2.

(Step 3)

The mixture of unreacted polyamine and water which was recovered by being distilled and concentrated in the process of the above removal operation was charged to a separable flask, and then water was removed by distillation whereby 149.4 g of residual was obtained. Purity of IPDA in the residual was 92%.

EXAMPLE 10

(Step 1)

817.2 g (6.0 mol) of MXDA and 2.9 g (0.13 mol) of lithium amide were charged to a flask similar as the one used in Example 1, and its interior temperature was raised to 80° C. in a nitrogen gas stream with stirring.

Then, keeping the interior temperature at 80° C., 625.2 g (6.0 mol) of styrene was added thereto dropwise continuously for 2 hours.

After completion of the dropwise addition of styrene, its interior temperature was maintained to 80° C. for 30 minutes, whereby 1441 g of reaction liquid containing an amino composition was obtained. The content of unreacted MXDA in the obtained reaction liquid was 15.8% by weight.

(Step 2)

1441 g of the reaction liquid thus obtained was charged to a flask similar as the one used in Example 1, and its interior pressure was reduced to 6.0 kPa. After stirring, the interior temperature was raised to 175° C. by heating.

After the interior temperature was reached to the prescribed temperature, steam with pressure of 49 kPa was introduced into the reaction apparatus and a removal operation of unreacted polyamine was carried out for 3 hours to remove unreacted polyamine in the form of a mixture of unreacted polyamine and water.

Then, the introduction of steam was stopped and the interior temperature and the degree of reduced pressure were kept as prescribed for 30 minutes.

Then, 29 g of "KYOWAAD 600s" as an alkali absorbent of the amount of 10 times equal parts by weight to the charged lithium amide was added thereto and stirred for 1 hour. Precipitate in the liquid in flask was removed by filtration, whereby 1179.3 g of amino composition J was obtained.

The content of unreacted MXDA in the obtained amino composition was 1.2% by weight. The content of 1-addition product was 53.0% by weight, the content of 2-addition product was 41.8% by weight and the content of 3-addition product was 4.0% by weight. The content of Lithium in the obtained amino composition was 1.2 ppm. The viscosity of the amino composition J was 64 MPa·s. The storage stability test was carried out with the amino composition J and the result was shown in Table 2.

(Step 3)

The mixture of unreacted polyamine and water which was recovered by being distilled and concentrated in the process of the above removal operation was charged to a separable flask, and then water was removed by distillation whereby 208.2 g of residual was obtained. Purity of MXDA in the residual was 92%.

TABLE 1

|  | Example 1 | Example 2 | Example 3 | Example 4 | Example 5 |
|---|---|---|---|---|---|
| Content of Lithium (ppm) | 0.7 | 0.7 | 0.7 | 1.2 | 1.2 |
| Content of Unreacted Polyamine (% by weight) | 0.9 | 1.2 | 1.9 | 1.6 | 0.9 |
| Initial Viscosity (MPa · s/25° C.) | 66 | 65 | 66 | 70 | 70 |
| Initial Appearance | Clear | Clear | Clear | Clear | Clear |
| Viscosity after 1 year (MPa · s/25° C.) | 66 | 65 | 66 | 70 | 70 |
| Appearance after 1 year | Clear | Clear | Clear | Clear | Clear |
| Storage stability | Good | Good | Good | Good | Good |

TABLE 2

|  | Example 6 | Example 7 | Example 8 | Example 9 | Example 10 |
|---|---|---|---|---|---|
| Content of Lithium (ppm) | 1.5 | 1.5 | 1.8 | 2.2 | 1.2 |
| Content of Unreacted Polyamine (% by weight) | 1.9 | 1.9 | 1.2 | 1.6 | 1.2 |
| Initial Viscosity (MPa · s/25° C.) | 35 | 116 | 168 | 108 | 64 |
| Initial Appearance | Clear | Clear | Clear | Clear | Clear |
| Viscosity after 1 year (MPa · s/25° C.) | 35 | 116 | 168 | 108 | 64 |
| Appearance after 1 year | Clear | Clear | Clear | Clear | Clear |
| Storage stability | Good | Good | Good | Good | Good |

COMPARATIVE EXAMPLE 1

(Step 1)

1453 g of reaction liquid containing an amino composition was obtained in the same manner as Example 1.

(Step 2)

1453 g of the reaction liquid thus obtained was charged to a 2L flask similar as the one used in Example 1 except that a nitrogen gas inlet was equipped instead of a steam inlet, and its interior pressure was reduced to 6.0 kPa. After stirring, the interior temperature was raised to 175° C. by heating.

After the interior temperature was reached to the prescribed temperature, nitrogen gas was introduced into the reaction apparatus and a removal operation of unreacted polyamine was carried out for 6 hours, whereby 1194.5 g of an amino composition K was obtained.

The content of unreacted MXDA in the obtained amino composition was 2.5% by weight. The viscosity of the amino composition K was 64 MPa·s. The storage stability test was carried out with the amino composition K and the result was shown in Table 3.

COMPARATIVE EXAMPLE 2

(Step 1)

817.2 g (6.0 mol) of MXDA and 2.9 g (0.13 mol) of lithium amide were charged to a flask similar as the one used in Example 1 and its interior temperature was raised to 80° C. in a nitrogen gas stream with stirring.

Then, keeping the interior temperature at 80° C., 625.2 g (6.0 mol) of styrene was added thereto dropwise continuously for 2 hours. After completion of the dropwise addition of styrene, its interior temperature was maintained to 80° C. for 30 minutes.

Then, 23.4 g (1.3 mol) of distilled water as the amount of 10 times equal mole to the charged lithium amide was added thereto and stirred for 1 hour. Precipitate in the liquid in flask was removed by filtration, whereby 1458 g of reaction liquid containing an amino composition was obtained. The content of unreacted MXDA in the obtained reaction liquid was 15.8% by weight. The content of Lithium in the obtained reaction liquid was 26.3 ppm.

(Step 2)

1458 g of the reaction liquid thus obtained was charged to a flask similar as the one used in Comparative Example 1, and its interior pressure was reduced to 6.0 kPa. After stirring, the interior temperature was raised to 175° C. by heating.

After the interior temperature was reached to the prescribed temperature, nitrogen gas was introduced into the reaction apparatus and a removal operation of unreacted polyamine was carried out for 6 hours, whereby 1170.1 g of an amino composition L was obtained.

The content of unreacted MXDA in the obtained amino composition was 3.1% by weight. The content of 1-addition product was 53.1% by weight, the content of 2-addition product was 42.0% by weight and the content of 3-addition product was 4.0% by weight. The viscosity of the amino composition L was 66 MPa·s. The storage stability test was carried out with the amino composition L and the result was shown in Table 3.

COMPARATIVE EXAMPLE 3

(Step 1)

853.2 g (6.0 mol) of 1,3-BAC and 3.0 g (0.13 mol) of lithium amide were charged to a flask similar as the one used in Example 1 and its interior temperature was raised to 80° C. in a nitrogen gas stream with stirring.

Then, after stirring the reaction mixture for 120 minutes at 80° C., 625.2 g (6.0 mol) of styrene was added thereto dropwise continuously for 2 hours while keeping the temperature at 80° C.

After completion of the dropwise addition of styrene, its interior temperature was maintained to 80° C. for 60 minutes.

Then, 23.4 g (1.3 mol) of distilled water as the amount of 10 times equal mole to the charged lithium amide was added thereto and stirred for 1 hour. Precipitate in the liquid in flask was removed by filtration, whereby 1462.2 g of reaction liquid containing an amino composition was obtained. The content of unreacted 1,3-BAC in the obtained reaction liquid was 15.1% by weight. The content of Lithium in the obtained reaction liquid was 33.2 ppm.

(Step 2)

1462.2 g of the reaction liquid thus obtained was charged to a flask similar as the one used in Comparative Example 1, and its interior pressure was reduced to 6.0 kPa. After stirring, the interior temperature was raised to 145° C. by heating.

After the interior temperature was reached to the prescribed temperature, nitrogen gas was introduced into the reaction apparatus and a removal operation of unreacted polyamine was carried out for 6 hours, whereby 1236.4 g of amino composition M was obtained.

The content of unreacted 1,3-BAC in the obtained amino composition was 3.5% by weight. The content of 1-addition product was 62.7% by weight, the content of 2-addition product was 33.3% by weight and the content of 3-addition product was 2.4% by weight. The viscosity of the amino composition M was 70 MPa·s. The storage stability test was carried out with the amino composition M and the result was shown in Table 3.

COMPARATIVE EXAMPLE 4

(Step 1)

412.7 g (4.0 mol) of DETA and 2.5 g (0.11 mol) of lithium amide were charged to a flask similar as the one used in Example 1 and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2 hours while keeping the temperature at 80° C.

After completion of the dropwise addition of styrene, its interior temperature was maintained to 80° C. for 60 minutes.

Then, 19.8 g (1.1 mol) of distilled water as the amount of 10 times equal mole to the charged lithium amide was added thereto and stirred for 1 hour. Precipitate in the liquid in flask was removed by filtration, whereby 840.6 g of reaction liquid containing an amino composition was obtained. The content of unreacted DETA in the obtained reaction liquid was 16.3% by weight. The content of Lithium in the obtained reaction liquid was 33.1 ppm.

(Step 2)

840.6 g of the reaction liquid thus obtained was charged to a flask similar as the one used in Comparative Example 1, and its interior pressure was reduced to 13.3 kPa. After stirring, the interior temperature was raised to 140° C. by heating.

After the interior temperature was reached to the prescribed temperature, nitrogen gas was introduced into the reaction apparatus and a removal operation of unreacted polyamine was carried out for 6 hours, whereby 602.5 g of amino composition N was obtained.

The content of unreacted DETA in the obtained amino composition was 2.8% by weight. The content of 1-addition product was 43.2% by weight, the content of 2-addition product was 45.0% by weight and the content of 3-addition product was 9.9% by weight. The viscosity of the amino composition N was 35 MPa·s. The storage stability test was carried out with the amino composition N and the result was shown in Table 3.

COMPARATIVE EXAMPLE 5

(Step 1)

584.8 g (4.0 mol) of TETA and 3.0 g (0.13 mol) of lithium amide were charged to a flask similar as the one used in Example 1 and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2 hours while keeping the temperature at 80° C.

After completion of the dropwise addition of styrene, its interior temperature was maintained to 80° C. for 60 minutes.

Then, 23.4 g (1.3 mol) of distilled water as the amount of 10 times equal mole to the charged lithium amide was added thereto and stirred for 1 hour. Precipitate in the liquid in flask was removed by filtration, whereby 1003 g of reaction liquid containing an amino composition was obtained. The content of unreacted TETA in the obtained reaction liquid was 16.3% by weight. The content of Lithium in the obtained reaction liquid was 24.8 ppm.

(Step 2)

1003 g of the reaction liquid thus obtained was charged to a flask similar as the one used in Comparative Example 1, and its interior pressure was reduced to 13.3 kPa. After stirring, the interior temperature was raised to 140° C. by heating.

After the interior temperature was reached to the prescribed temperature, nitrogen gas was introduced into the reaction apparatus and a removal operation of unreacted polyamine was carried out for 6 hours, whereby 816.2 g of amino composition O was obtained.

The content of unreacted TETA in the obtained amino composition was 3.0% by weight. The content of 1-addition product was 59.8% by weight, the content of 2-addition product was 38.4% by weight and the content of 3-addition product was 1.8% by weight. The viscosity of the amino composition O was 116 MPa·s. The storage stability test was carried out with the amino composition O and the result was shown in Table 4.

COMPARATIVE EXAMPLE 6

(Step 1)

681.2 g (4.0 mol) of IPDA and 3.3 g (0.14 mol) of lithium amide were charged to a flask similar as the one used in Example 1 and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2.5 hours while keeping the temperature at 80° C.

After completion of the dropwise addition of styrene, its interior temperature was maintained to 80° C. for 60 minutes.

Then, 25.2 g (1.4 mol) of distilled water as the amount of 10 times equal mole to the charged lithium amide was added thereto and stirred for 1 hour. Precipitate in the liquid in flask was removed by filtration, whereby 1102 g of reaction liquid containing an amino composition was obtained. The content of unreacted IPDA in the obtained reaction liquid was 14.6% by weight. The content of Lithium in the obtained reaction liquid was 41.0 ppm.

(Step 2)

1102 g of the reaction liquid thus obtained was charged to a flask similar as the one used in Comparative Example 1, and its interior pressure was reduced to 13.3 kPa. After stirring, the interior temperature was raised to 170° C. by heating.

After the interior temperature was reached to the prescribed temperature, nitrogen gas was introduced into the reaction apparatus and a removal operation of unreacted polyamine was carried out for 6 hours, whereby 902.5 g of amino composition P was obtained.

The content of unreacted IPDA in the obtained amino composition was 2.6% by weight. The content of 1-addition product was 59.8% by weight and the content of 2-addition product was 39.0% by weight. The viscosity of the amino composition P was 168 MPa·s. The storage stability test was carried out with the amino composition P and the result was shown in Table 4.

COMPARATIVE EXAMPLE 7

(Step 1)

617.2 g (4.0 mol) of NBDA and 3.1 g (0.14 mol) of lithium amide were charged to a flask similar as the one used in Example 1 and its interior temperature was raised to 80° C. in a nitrogen gas stream with stirring.

Then, after stirring the reaction mixture for 120 minutes at 80° C., 416.8 g (4.0 mol) of styrene was added thereto dropwise continuously for 2.5 hours while keeping the temperature at 80° C.

After completion of the dropwise addition of styrene, its interior temperature was maintained to 80° C. for 120 minutes.

Then, 25.2 g (1.4 mol) of distilled water as the amount of 10 times equal mole to the charged lithium amide was added thereto and stirred for 1 hour. Precipitate in the liquid in flask was removed by filtration, whereby 1011 g of reaction liquid containing an amino composition was obtained. The content of unreacted NBDA in the obtained reaction liquid was 15.5% by weight. The content of Lithium in the obtained reaction liquid was 40.5 ppm.

(Step 2)

1011 g of the reaction liquid thus obtained was charged to a flask similar as the one used in Comparative Example 1, and its interior pressure was reduced to 1.3 kPa. After stirring, the interior temperature was raised to 120° C. by heating.

After the interior temperature was reached to the prescribed temperature, nitrogen gas was introduced into the reaction apparatus and a removal operation of unreacted polyamine was carried out for 6 hours, whereby 822.3 g of amino composition Q was obtained.

The content of unreacted NBDA in the obtained amino composition was 4.2% by weight. The viscosity of the amino composition Q was 108 MPa·s. The storage stability test was carried out with the amino composition Q and the result was shown in Table 4.

TABLE 3

| | Comparative Example 1 | Comparative Example 2 | Comparative Example 3 | Comparative Example 4 |
|---|---|---|---|---|
| Content of Lithium (ppm) | 0.7 | 26.3 | 33.2 | 33.1 |

TABLE 3-continued

| | Comparative Example 1 | Comparative Example 2 | Comparative Example 3 | Comparative Example 4 |
|---|---|---|---|---|
| Content of Unreacted Polyamine (% by weight) | 2.5 | 3.1 | 3.5 | 2.8 |
| Initial Viscosity (MPa · s/25° C.) | 64 | 66 | 70 | 35 |
| Initial Appearance | Clear | Clear | Clear | Clear |
| Viscosity after 1 year (MPa · s/25° C.) | 64 | 650 | 1180 | 560 |
| Appearance after 1 year | Clear | Clouded | Clouded | Clouded |
| Storage stability | Good | Poor | Poor | Poor |

TABLE 4

| | Comparative Example 5 | Comparative Example 6 | Comparative Example 7 |
|---|---|---|---|
| Content of Lithium (ppm) | 24.8 | 41.0 | 40.5 |
| Content of Unreacted Polyamine (% by weight) | 3.0 | 2.6 | 4.2 |
| Initial Viscosity (MPa · s/25° C.) | 116 | 168 | 108 |
| Initial Appearance | Clear | Clear | Clear |
| Viscosity after 1 year (MPa · s/25° C.) | 1520 | 2200 | 1620 |
| Appearance after 1 year | Clouded | Clouded | Clouded |
| Storage stability | Poor | Poor | Poor |

As clear from the above Examples, according to the process for producing an amino composition of the present invention by addition reaction between a polyamine and an unsaturated hydrocarbon compound, an amino composition wherein the content of unreacted polyamine is not more than 2% by weight can be obtained inexpensively and easily without accompanying unfavorable changes such as coloration. In addition, an amino composition wherein the content of alkali metal is not more than 10 ppm can be obtained easily.

The amino composition obtained by the process of the present invention has advantages not only that it is excellent in storage stability but also that, when used as an epoxy resin curing agent, it can provide an epoxy resin coating film having excellent appearance wherein unfavorable phenomena such as whitening and tackiness do not readily occur.

What is claimed is:

1. A process for producing an amino composition by addition reaction between a polyamine selected from the group consisting of the following (a) to (c) and an unsaturated hydrocarbon compound in the presence of a strongly basic alkali metal catalyst to obtain an amino composition containing not more than 2% by weight of unreacted polyamine, which at least comprises the following steps:

(A) a step of conducting addition reaction between the polyamine and an unsaturated hydrocarbon compound in the presence of a strongly basic alkali metal catalyst to obtain a reaction liquid containing an amino composition (addition reaction-step), (B) a step of removing unreacted polyamine from the reaction liquid containing an amino composition obtained by said addition reaction-step (A) in the form of a mixture of water and unreacted polyamine by steam stripping under reduced pressure in the range of 2 to 50 mmHg to obtain an amino composition wherein the content of unreacted polyamine is not more than 2% by weight (steam stripping-step);

(a) polyamines represented by the formula (1) wherein A is a phenylene group or a cyclohexylene group,

$$H_2N-CH_2-A-CH_2-NH_2 \qquad (1)$$

(b) polyamines represented by the formula (2) wherein n is 2 to 5,

$$H_2N-(CH_2CH_2NH)_n-H \qquad (2)$$

(c) cyclic aliphatic polyamines having at least nine carbon atoms, at least two amino groups and at least three active hydrogen atoms derived from said amino groups.

2. The process according to claim 1, which further comprises a step of removing a strongly basic alkali metal catalyst or the alkali metal compound thereof to reduce the content of alkali metal in said amino composition to 10 ppm or less (catalyst-removing-step) to obtain an amino composition containing not more than 2% by weight of unreacted polyamine and not more than 10 ppm of alkali metal.

3. The process according to claim 2, which at least comprises the following steps:

(A') a step of firstly conducting addition reaction between a polyamine and an unsaturated hydrocarbon compound in the presence of a strongly basic alkali metal catalyst to obtain a reaction liquid containing an amino composition (addition reaction-step), and then removing said strongly basic alkali metal catalyst from said reaction liquid to reduce the content of alkali metal in said reaction liquid to 10 ppm or less (catalyst-removing-step), (B) a step of removing unreacted polyamine from said reaction liquid containing alkali metal not more than 10 ppm obtained by said step (A') in the form of a mixture of water and unreacted polyamine by steam stripping to obtain an amino composition wherein the content of unreacted polyamine is not more than 2% by weight and the content of alkali metal is not more than 10 ppm (steam stripping-step).

4. The process according to claim 3, wherein said unsaturated hydrocarbon compound is selected from the group consisting of a cyclic unsaturated hydrocarbon compound having at least one benzene ring and/or cyclohexane ring and a straight-chain unsaturated hydrocarbon compound having 2 to 10 carbon atoms.

5. The process according to claim 2, which at least comprises the following steps:

(A) a step of conducting addition reaction between the polyamine and an unsaturated hydrocarbon compound in the presence of a strongly basic alkali metal catalyst to obtain a reaction liquid containing an amino composition (addition reaction-step), (B) a step of firstly removing unreacted polyamine from said reaction liquid containing an amino composition obtained by said step (A) in the form of a mixture of water and unreacted polyamine by steam stripping to obtain a reaction liquid containing an amino composition wherein the content of unreacted polyamine is not more than 2% by weight (steam stripping-step), and then removing hydroxide derived from said strongly basic alkali metal catalyst from said reaction liquid containing an amino composition wherein the content of unreacted polyamine is not more than 2% by weight to obtain an amino composition wherein the content of unreacted polyamine is not more than 2% by weight and the content of alkali metal is not more than 10 ppm (catalyst-removing-step).

6. The process according to claim 5, wherein said unsaturated hydrocarbon compound is selected from the group consisting of a cyclic unsaturated hydrocarbon compound having at least one benzene ring and/or cyclohexane ring and a straight-chain unsaturated hydrocarbon compound having 2 to 10 carbon atoms.

7. The process according to claim 1, wherein said unsaturated hydrocarbon compound is selected from the group consisting of a cyclic unsaturated hydrocarbon compound having at least one benzene ring and/or cyclohexane ring and a straight-chain unsaturated hydrocarbon compound having 2 to 10 carbon atoms.

8. The process according to claim 2, wherein said unsaturated hydrocarbon compound is selected from the group consisting of a cyclic unsaturated hydrocarbon compound having at least one benzene ring and/or cyclohexane ring and a straight-chain unsaturated hydrocarbon compound having 2 to 10 carbon atoms.

* * * * *